United States Patent [19]

Peerless

[11] 4,326,512
[45] Apr. 27, 1982

[54] COMPOSITE VENTILATION TUBE FOR THE MIDDLE EAR

[76] Inventor: Sidney A. Peerless, 2650 Kipling Ave., Cincinnati, Ohio 45239

[21] Appl. No.: 121,417

[22] Filed: Feb. 14, 1980

[51] Int. Cl.³ .............................................. A61F 11/00
[52] U.S. Cl. .................................. 128/151; 128/350 R
[58] Field of Search ............... 128/350 R, 350 V, 151, 128/152, 348; 181/130, 134, 135

[56] References Cited

U.S. PATENT DOCUMENTS

| | | | |
|---|---|---|---|
| 834,259 | 10/1906 | Campbell | 181/134 |
| 886,790 | 5/1908 | Frank | 128/151 |
| 1,016,877 | 2/1912 | Elliott . | |
| 1,045,917 | 12/1912 | Valiquet | 128/151 |
| 1,497,722 | 6/1924 | Holst-Grubbe | 128/350 R |
| 2,427,664 | 9/1947 | Dunbar et al. | 128/151 |
| 2,672,863 | 3/1954 | Leight | 128/152 |
| 3,333,588 | 8/1967 | Schulte | 128/350 R |
| 3,530,860 | 9/1970 | Majoros | 128/305 |
| 3,807,409 | 4/1974 | Paparella et al. | 128/350 R |
| 3,871,380 | 3/1975 | Heros | 128/350 R |
| 3,916,873 | 11/1975 | Wasserman | 128/1 R |
| 3,948,271 | 4/1976 | Akiyama | 128/350 R |
| 3,976,081 | 8/1976 | Lapidot | 128/350R |
| 3,982,545 | 9/1976 | Silverstein | 128/350 R |
| 4,193,399 | 3/1980 | Robinson | 128/348 X |

*Primary Examiner*—Michael H. Thaler
*Attorney, Agent, or Firm*—Wood, Herron & Evans

[57] ABSTRACT

A composite ventilation tube is disclosed which is specifically useful for ventilating the middle ear. The tube assembly includes an outer tube formed of inert, slightly flexible material, such as Teflon or polyethylene, which includes an elongated thin-walled tubular section having a central bore and a plurality of axially spaced, angularly staggered transverse openings. A flange is formed at one end of the tube, the plane of the flange being disposed at an acute angle relative to the axis of the tube with at least one portion of the flange terminating closely adjacent to the tubular wall. A cylindrical piston fits within the tube and includes a slightly enlarged head engaging the open, outer end of the tube. The piston is formed of porous polyethylene having pores of the order of 20 to 50 microns.

6 Claims, 4 Drawing Figures

COMPOSITE VENTILATION TUBE FOR THE MIDDLE EAR

FIELD OF THE INVENTION

This invention relates to medical devices and is particularly directed to ventilation tubes. More particularly, the present invention relates to ventilation tubes for the middle ear. The ventilation tube is adapted to be inserted through the tympanic membrane to provide ventilation through that membrane to the middle ear and to provide means for equalizing pressure between the middle ear and outer ear.

BACKGROUND OF THE INVENTION

It has become common practice to treat various problems of the middle ear by providing some means of continuously aerating the middle ear through the tympanic membrane. This has been accomplished by inserting ventilation tubes through the tympanic membrane or through a bony area adjacent thereto. Various ventilation and drain tubes which have been previously proposed are shown in U.S. Pat. Nos. 3,530,860; 3,807,409; 3,871,380; 3,916,873; 3,948,271; 3,982,454 and 3,976,081. These prior art ventilation tubes are each subject to one or more serious defects which it is the object of the present invention to overcome.

More particularly, one of the principal defects of the prior art ventilation tubes is that they do not effectively seal off the inner ear from the entrance of water. If water enters the inner ear through such a tube, it can lead to aggravated middle ear infection. As a consequence, patients who have heretofore been fitted with inner ear ventilation tubes have been restricted in their activities, particularly those involving water. Thus, such patients could not normally go swimming.

A still further difficulty with prior art ventilation tubes is that they provided no ready means for changing the filter element. For example, if a tube has been in place for a substantial length of time, the tympanic membrane may tend to grow into the tube. With prior art ventilation tubes, it was necessary to replace the entire tube which consumed a substantial amount of time and entails considerable discomfort to the patient.

OBJECTS OF THE INVENTION

The principal object of the present invention is to provide a novel ventilation tube for the middle ear which is effective to provide optimum aeration of the inner ear, but which will prevent water from entering the middle ear. Thus, a person fitted with the present ventilation tube can participate in their full range of normal activities, including swimming, without developing an aggravated inner ear infection due to the entrance of water into that cavity.

Another object of the present invention is to provide a novel middle ear ventilation tube which is easily inserted and yet will remain in place for long periods of time, e.g., in excess of six months, sufficient for treatment of many problems of the middle ear.

A still further object of the present invention is to provide a ventilation tube for the middle ear which utilizes only a minimum amount of material disposed within the middle ear and which does not result in any objectionable pressure on the wearer's eardrum.

A still further object of the present invention is to provide a composite ventilation tube including an outer tube which is the sole member in contact with the user's tissue. The composite tube further includes an inner piston-like member which selectively permits air flow while preventing passage of water. This inner piston is normally shielded from contact with the user's tissue and, hence, does not irritate it even if its material would normally be an irritant.

Yet another object of the present composite ventilation tube is that the piston can be removed while leaving the outer tube in place. Thus, the piston can be displaced outwardly by a pressure build-up in the inner ear to automatically alleviate some of the user's discomfort. Moreover, the piston can be removed and replaced if the patient's tympanic membrane should start to grow into the pores of the piston. Since the outer tube remains in place, replacement of the piston can be done rapidly and without discomfort to the patient.

SUMMARY OF THE INVENTION

The present invention is predicated upon the concept of providing a composite ventilation tube for the middle ear comprising an outer tube including thin-walled tubular section having a central bore and a plurality of axially spaced, angularly staggered transverse openings. In the preferred embodiment, the tubular section is of a circular cross-section and has a transverse flange formed at one end thereof. An axial bore extends through the entire length of the tubular member and through the flange which is adapted to be disposed within the middle ear in abutment with the tympanic membrane. The outer tube is made from a material, such as polyethylene or Teflon, which is compatible with human tissue.

In accordance with the present invention, the flange is disposed at an acute angle, preferably of the order of 45°, with the axis of the tube. This flange is preferably U-shaped with one edge terminating closely adjacent to the wall of the tube, the edge extending generally at right angles to the major diameter of the tube. The outline configuration of the flange is of a generally U-shape. I have empirically determined that this flange configuration is effective, with a minimum amount of material in the inner ear, to retain the outer tube in place over substantial periods of time.

The outer tube carries a porous piston-like inner member which permits air to pass between the outer and inner ears, but prevents water from entering the inner ear. In a preferred embodiment, this piston member is formed from porous polyethylene having pores of the order of 20–50 microns in size. The inner member includes a cylindrical stem portion which fits within the outer tube and an enlarged head which engages the end of the tube to limit inward movement of the piston member. This head provides a ready means for grasping the piston and for removing it while leaving the outer tube in place.

These and other objects and advantages of the present invention will become more readily apparent from a consideration of the following detailed description of the drawings illustrating a preferred embodiment of the invention.

DETAILED DESCRIPTION OF DRAWINGS

Figure 1:
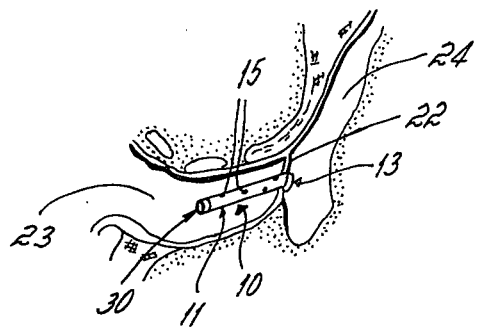
FIG. 1 is a sectional view of an ear as viewed from the right side of the head, the ear being fitted with a composite ventilation tube assembly of the present invention.
Figure 2:
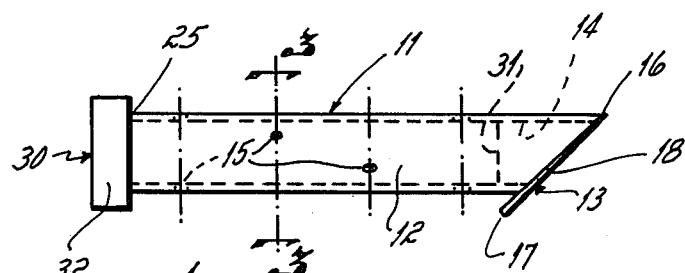
FIG. 2 is a side elevational view of a composite ventilation tube assembly embodying the present invention.
Figure 3:
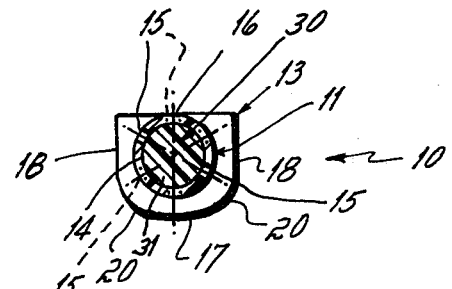
FIG. 3 is a cross-sectional view taken along line 3—3 of FIG. 2.
Figure 4:
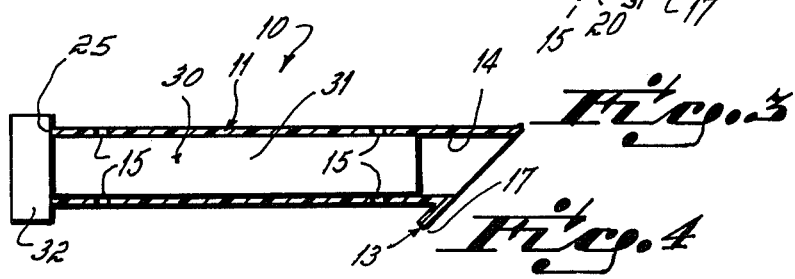
FIG. 4 is a longitudinal cross-sectional view of the composite ventilation tube assembly of FIG. 2.

One preferred form of composite middle ear ventilation tube assembly 10 constructed in accordance with the principles of the present invention is illustrated in FIGS. 2 and 3, and the manner in which such a tube is inserted in a patient's ear is shown in FIG. 1. The composite tube assembly includes an outer tube 11 made of a suitable material which is inert, compatible with human tissue and slightly flexible, such as polyethylene or Teflon.

As shown in FIG. 2, the outer tube 11 comprises an elongated tubular section 12 and a flange 13 extending transversely of one end of the tubular section. The tubular section 12 is preferably of circular configuration and is relatively thin-walled. An axial bore 14 extends the complete length of the outer tubular member through both tubular section 12 and flange 13. Tubular section 12 is provided with a plurality of transverse, or radial, openings 15 of approximately one millimeter in diameter. Openings 15 are spaced axially along tubular section 12 and also are arranged at progressively staggered angular positions. While the exact dimensions of the tube may vary, one preferred embodiment is approximately one centimeter long. It will be appreciated, however, that the tubular section can be cut off to the length required and, hence, in use may have a shorter length, e.g., 5–6 millimeters. The outer diameter of the tube section 12 is approximately two millimeters. The inner diameter of the tubular section 12 is approximately 1.1 millimeters.

As is best shown in FIG. 2, flange 13 extends transversely of one end of tubular section 12. The flange is disposed at an acute angle to the axis of the tube and central bore 14. This angle is approximately 45° to the axis of the tube. Flange 13 does not extend a uniform distance outwardly from the tubular section 12. Rather, at the apex region 16 of the tube the flange terminates closely adjacent the tubular wall. One edge 17 of the flange extends in a direction generally tangential of the wall in the apex region. The outline configuration of the flange is generally U-shaped with side walls 18 extending generally perpendicular to edge 17. The side edges 18 are interconnected by an arcuate edge 20. In the preferred embodiment, the thickness of the flange decreases slightly from edge 17 toward edge 16. However, it is contemplated that a flange of uniform thickness can be employed if desired.

The composite ventilation tube assembly further includes a piston member 30. Piston member 30 is configurated to form a stem portion 31 of cylindrical cross-section and an enlarged head 32. Stem portion 31 is of substantially the same inner diameter as the diameter of bore 14 and the length of the stem portion is approximately the same as the minimum length of bore 14. Consequently, when the stem 31 is inserted in bore 14, it substantially fills the bore and is frictionally held in place against accidental dislodgement. Head 32 is of larger diameter than the bore 14 and is preferably of slightly larger diameter than the outer diameter of the tubular section 12. When the piston member is assembled with the outer tubular member, head 32 is adapted to abut the end wall 25 of tubular section 12 to limit the amount of insertion of stem 31 into the tubular member.

Piston member 30 is formed of a microporous plastic material which permits passage of air, but does not permit passage of water. Suitable forms of microporous plastic materials are produced by Porex Division of Glassrock Company of Fairborn, Georgia, and General Polymeric Corporation of West Reading, Pennsylvania. This material is formed by compressing particles of polyethylene resin to form a material having interconnected open cell structures with pores of the order of from 20–50 microns.

In use, the composite ventilation tube is adapted to be inserted in a hole formed in the tympanic membrane 22 of a patient's ear. This membrane separates the outer ear canal 23 from the middle ear 24. After insertion, the outer tube 11 is pulled gently outwardly until flange 13 fits snugly against the tympanic membrane. In this position, the composite tube is effective to provide aeration from the middle ear with air passing through central bore 14 and radial openings 15 of the outer tube and through the porous openings in piston member 30. In the event that it is desired to remove piston member 30, it is only necessary to grasp head 32 and withdraw the member outwardly until stem 31 becomes disengaged from bore 14. The outer sleeve 11 remains in place. Piston member 30 can be replaced, or a new one inserted, by merely pressing stem 31 inwardly through bore 14 of the outer tube until head 32 engages the end of the tube.

The present tube is advantageous in that there is a minimum amount of material disposed within the middle ear. Nevertheless, the present outer ventilation tube is effectively retained in place for a long period, e.g., in excess of six months, before it is ejected from the ear. This time is sufficient for the treatment of many conditions. The inner piston member 30 is likewise held in place by its frictional engagement with the outer tube. Nevertheless, if excessive pressure should build up in the inner ear, piston 30 can be displaced outwardly to afford relief to the patient. The present tube provides optimum aeration of the ear and is effective to continue to provide aeration, while at the same time preventing entrance of water into the inner ear even if the patient is engaging in water sports, such as swimming.

From the above disclosure of the general principles of the present invention and the preceding description of a preferred embodiment, those skilled in the art will readily comprehend various modifications to which the invention is susceptible. Therefore, I desire to be limited only by the scope of the following claims.

Having described my invention, I claim:

1. A composite ventilation tube assembly for the middle ear, said composite ventilation tube comprising:
   an outer tube formed from a slightly flexible inert material, said outer tube including:
      a thin-walled tubular section having a central bore extending completely therethrough;
      an outwardly extending flange formed at one end of the tubular section; and
      a plurality of transverse openings formed in the walls of said tubular section in fluid communication with said central bore;
   a piston member formed of microporous plastic material, said piston member including:
      a stem portion disposed within said tubular section and in frictional engagement therewith; and a head disposed outwardly of said bore and adapted for engagement with the end of said tubular section;

said piston member being displaceable axially outwardly away from said flange in response to buildup in pressure within the middle ear.

2. The composite ventilation tube of claim 1 in which said piston member is formed of porous polyethylene.

3. The composite ventilation tube of claim 2 in which said piston member has pores of the order of 20–50 microns in size.

4. The composite ventilation tube of claim 1 in which said flange is disposed at an angle relative to the axis of said bore.

5. The composite ventilation tube of claim 1 in which said openings are spaced longitudinally along said tubular section and are disposed at staggered angular positions around the wall of said tubular section.

6. The composite ventilation tube of claim 5 in which said flange is of generally U-shaped outline configuration and terminates closely adjacent to the wall at an apex region of said tube and extends at substantially greater distances from said tube at other portions of said wall.

* * * * *